United States Patent [19]

Hengartner

[11] 4,296,259
[45] Oct. 20, 1981

[54] PREPARATION OF A 1,4-PENTADIEN-3-OL

[75] Inventor: Urs Hengartner, Roseland, N.J.

[73] Assignee: Hoffmann-La Roche Inc., Nutley, N.J.

[21] Appl. No.: 157,574

[22] Filed: Jun. 9, 1980

Related U.S. Application Data

[62] Division of Ser. No. 24,296, Mar. 27, 1979, abandoned.

[51] Int. Cl.³ .......................................... C07C 49/743
[52] U.S. Cl. ............................ 568/378; 260/345.9 R; 568/606; 568/668; 568/824; 568/363; 568/347
[58] Field of Search ................ 568/363, 357, 378, 347

[56] References Cited

U.S. PATENT DOCUMENTS 4,083,812 4/1978 Moupetit et al. .................. 568/363
4,098,827 7/1978 Rosenberger ...................... 568/348
4,225,694 9/1980 Dalton et al. ...................... 568/363

Primary Examiner—Natalie Trousof
Assistant Examiner—James H. Reamer
Attorney, Agent, or Firm—Jon S. Saxe; George M. Gould; William H. Epstein

[57] ABSTRACT

A new process for preparing 1-(3-oxo-2,6,6-trimethyl-1-cyclohexen-1-yl)-3-methyl-1,4-pentadien-3-ol, a intermediate for canthaxanthin, from hydroxy-β-ionone.

1 Claim, No Drawings

PREPARATION OF A 1,4-PENTADIEN-3-OL

This is a division of application Ser. No. 24,296 filed Mar. 27, 1979, now abandoned.

BACKGROUND

In U.S. Pat. No. 4,098,827, July 4, 1978, Rosenberger, the compound 1-(3-oxo-2,6,6-trimethyl-1-cyclohexen-1-yl)-3-methyl-1,4-methyl-1,4-pentadien-3-ol which has the formula:

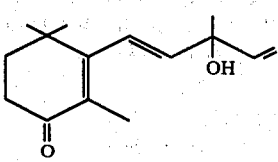

I has been prepared from a compound of the formula:

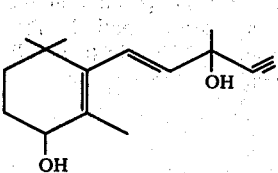

II by first reducing the compound of formula II to produce:

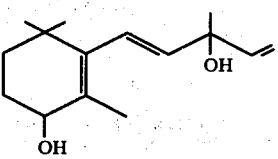

III and then oxidizing the compound of formula III to produce a compound of formula I. A disadvantage of this process is that the compound of the formula I is produced as an impure mixture. Since the compound of formula I is an intermediate for the known food coloring agent, canthaxanthin, which must be utilized in food in pure form, it is important to produce the intermediate in as pure a form as possible. It has been found that if the compound of formula I is produced from the compound of formula II via the intermediate of formula III, the compound of formula I must be purified by conventional means before it can be used in the further synthesis of commercially acceptable canthaxanthin.

SUMMARY OF INVENTION

In accordance with this invention, it has been found that when the compound of formula I is produced from the compound of formula II via an intermediate

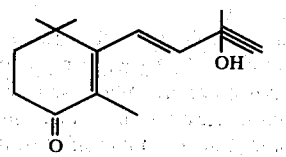

IV the compound of formula I is prepared in purity of at least 96% without the necessity of extraneous purification procedures. By utilizing the procedure of this invention, the time consumming and costly procedures involved in purifying intermediates in the production of canthaxanthin is substantially eliminated. Furthermore, utilizing the procedure of this invention, the compound of formula I is produced in a purity of at least 96%. In fact, this purity is obtained no matter how impure the starting material of formula II is utilized. Hence, the process of this invention allows one to utilize impure starting materials to obtain a pure intermediate without the necessity of utilizing expensive and time consumming purification techniques.

In accordance with another embodiment of this invention, the compounds of the formula II is prepared in high yields from hydroxy beta-ionone, i.e. a compound of formula

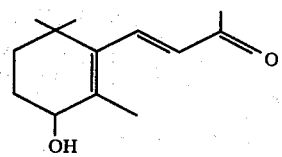

V by means of protecting the hydroxy group on the cyclohexene moiety prior to ethynylation.

DETAILED DESCRIPTION

In accordance with this invention, the compound of formula I is produced from the compound of formula II by first oxidizing the compound of formula II to the compound of formula IV, crystallizing the compound of formula IV from the reaction medium and then selectively reducing the compound of formula IV. The compound of formula II is oxidized to the compound of formula IV by treatment with an oxidizing agent. Any conventional oxidizing agents can be utilized to affect this conversion. Among the preferred oxidizing agents are included maganese dioxide and the chromate oxidizing agents such as Jones reagent. Any of the conditions conventional in carrying out this oxidation utilizing these reagents can be utilized in this conversion.

Among the preferred methods for carrying out the conversion of the compound of formula II to the compound of formula IV is by oxidation with an aluminum alkoxide in the presence of acetone. Any conventional aluminum alkoxide such as the aluminum lower alkoxide, i.e. those alkoxides which contain from 1 to 7 carbon atoms, can be utilized. Among the preferred aluminum alkoxides are included aluminum isopropoxide and aluminum t-butoxide. In carrying out this reaction, the aluminum alkoxide can be present in catalytic quantities, i.e. at least 0.1 mole percent based upon the moles of the compound of formula II. If desired, the aluminum isoproxide can be present in an amount of 100 mole percent based upon the moles of the compound of formula II. In fact, any excess of the aluminum alkoxide will not deleteriously affect this reaction. However, for economics, it is generally preferred to utilize the aluminum alkoxide in an amount of from 0.1 mole percent to 100 mole percent based upon the moles of the compound of formula II.

Generally, the oxidation with the aluminum alkoxide and acetone is carried out utilizing acetone as the organic solvent medium. If desired, the reaction medium can contain an additional solvent such as benzene and toluene. In fact, any inert organic solvent can be utilized in a mixture with the acetone. On the other hand, the reaction can be carried out in acetone without the presence of an inert organic solvent. Generally, this reaction is carried out at a reflux temperature of the reaction mixture.

In accordance with this invention, the compound of formula IV is produced as a crystalline material by the oxidation of the compound of formula II. The compound of the formula IV can be readily separated from the reaction mixture in which it is formed. Any conventional method of crystallization can be used to produce the compound of formula IV as a crystalline material. In accordance with the invention, the compound of formula IV can be easily crystallized from conventional non-polar solvents. Among the preferred non-polar solvents are included hexane, petroleum ether, etc. Therefore, the compound of formula IV can be recovered from the reaction mixture which is utilized in the oxidation of the compound of formula II as a crystalline material.

In accordance with this invention, the compound of formula IV is converted to the compound of formula I by partially hydrogenating the compound of the formula IV isolated in crystalline form from the reaction medium. Any conventional method of partially hydrogenating the compound of the formula IV can be utilized to affect this conversion. Any of the catalysts conventionally used for partially hydrogenating triple bonds to a double bond can be used in this conversion. Among the preferred catalysts for use in this reaction are the poisoned palladium catalysts (Lindlar catalysts) such as the type disclosed in the publication Helvetica Chimica Acta, 35, 446 (1952). In carrying out this reaction, the compound of formula IV is dissolved in an inert organic solvent. Any conventional inert organic solvent can be utilized. Among the preferred inert organic solvents are included ethyl acetate, toluene, petroleum ether, methylene chloride, etc. If desired, further conventional catalyst poisons such as 1,2-bis-(2-hydroxyethylthio)-ethane can be utilized to further deactivate the catalyst. In carrying out this reaction, temperature and pressure are not critical and this reaction can be carried out at room temperature and atmospheric pressure. If desired, higher or lower temperatures can be utilized. Generally, it is preferred to utilize a temperature of from 10° C. to 70° C. in carrying out this reaction.

In accordance with this invention, the compound of formula I which is produced by this selective hydrogenation is obtained in a purity of at least 96%.

In accordance with another embodiment of this invention, the compound of formula V is converted to the compound of formula II via the following intermediates:

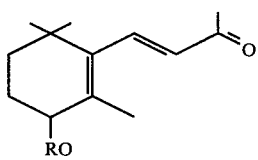

VII

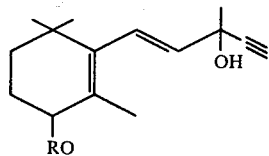

VIII wherein R taken together with its attached oxygen atom forms a hydrolyzable ether protecting group.

In the compounds of formulae VII and VIII, R can be any conventional ether protecting group. Among the preferred ether protecting groups are included benzyl, t-butyl, tetrahydropyranyl, and

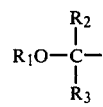

wherein $R_1$ is lower alkyl group containing from 1 to 7 carbon atoms such as methyl, ethyl, isopropyl, n-butyl, t-butyl, etc. wherein $R_2$ and $R_3$ are hydrogen or lower alkyl.

In forming the ether group,

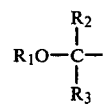

the compound of formula V is reacted with a compound of the formula

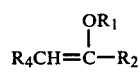

wherein $R_1$ and $R_2$ are as above; and $R_4$ is hydrogen or lower alkyl containg from 1 to 6 carbon atoms. This etherification reaction is carried out in the presence of a strong acid. Any conventional strong acid can be utilized in carrying out this reaction. Among the preferred acids are included the strong inorganic acids such as the hydrohalic acid, i.e. hydrogen bromide, as well as the other strong inorganic acids such as sulfuric. Among the preferred strong organic acids are included para-toluenesulfonic acid. Generally, this reaction is carried out in the presence of an inert organic solvent. Among the preferred organic solvents are included aprotic solvent which is tetrahydrofuran, dimethoxyethane, etc. On the other hand, the compound of formula V can be converted to the compound of formula VII by any conventional method of etherification. Among the preferred methods is to react the compound of formula V with alcohol or a reactive derivative thereof such as a halide to form the compound of formula VII utilizing conditions conventional in such etherification reactions.

The compound of formula VII is converted to the compound of formula VIII by treating a compound of formula VII with lithium acetylide. Any of the conditions conventional in reacting a ketone with an acetylide to form an addition product can be utilized in accordance with this invention. The compound of formula VIII is converted to the compound of formula II by aqueous acidic hydrolysis. Any conventional method of aqueous acidic hydrolysis can be utlized in carrying out this reaction. Among the preferred methods is by treating the compound of formula VIII with aqueous strong inorganic acids such as aqueous hydrochloric acid, aqueous sulfuric acid, aqueous hydrobromic acid, etc. In carrying out this reaction, temperature and pressures are not critical and this reaction can be carried out at room temperature and atmospheric pressure. Generally, it is preferred to use temperature in the range of from 0° C. to 50° C.

In accordance with this invention, the compound of formula V is converted to the compound of formula II through protecting the hydroxy group on the cyclohexene moiety in yields of about twice that obtained by directly ethynylating the compound of formula V with sodium acetalide in accordance with the procedure disclosed in U.S. Pat. No. 4,098,327. It is unexpectedly discovered that by protecting the hydroxy moiety on the compound of formula V, the yield of the compound of formula II is substantially increased.

In accordance with another embodiment of this invention, the compound of formula V can be converted to the compound of formula II by reacting the compound of formula V with acetylene in the presence of an alkali metal hydroxide in liquid ammonia at a temperature of from about −40° to about +30°. Any conventional alkali metal hydroxide in this process with sodium and potassium hydroxide being preferred and potassium hydroxide being especially preferred. In accordance with this step, the reaction is preferably carried out in a temperature range of from about −30° C. to about +5° C., preferably at about 0° C. and at pressures varying from 1 atmosphere to about 9.0 atmospheres, preferably 8 atmospheres.

The alkali metal hydroxide is generally employed in this reaction in catalytic amounts from about 0.1 mole % to about 20 mole %, preferably an amount of 10 mole % based upon the compound of formula V. The alkali metal hydroxide may be employed in larger amounts, i.e. up to 100 mole percent, although no significant advantages are gained thereby. The alkali metal hydroxide is generally used in aqueous or lower alkanol solutions. The lower alkanol as used herein designates straight and branched chained alcohol having from 1 to 7 carbon atoms. The preferred lower alkanol solution employed herein is a methanol solution. After carrying out this reaction, the remaining amount of catalysts can be neutralized with a mineral acid or a lower alkanoic acid. The preferred acids that may be employed in this neutralization are sulfuric, nitric, hydrochloric, acetic and the like.

The invention is further illustrated by the following examples

EXAMPLE 1

A one liter three-necked flask equipped with thermometer, mechanical stirrer and dropping funnel was charged under nitrogen with 208.3 g (1.0 mol) of 4-(3-hydroxy-2,6,6-trimethyl-1-cyclohexen-1-yl)-3-buten-2-one
100.8 g (1.4 mol) of isopropenyl methyl ether and
160 ml of tetrahydrofuran. The mixture was stirred until a homogeneous solution was obtained and then cooled in an icebath to 3° C. Then a solution of 1.4 g (7.4 mmol) of p-toluene sulfonic acid monohydrate in 20 ml of tetrahydrofuran was added at 3°–6° over 1¼ hr. After the mixture had been stirred for an additional 20 min at 3°
3.0 ml of triethylamine was added. The clear, light yellow solution containing 4-[3-(1-methoxy-1-methylethoxy)-2,6,6-trimethyl-1-cyclohexen-1-yl]-3-buten-2-one was kept in the refrigerator before it was used.

EXAMPLE 2

A three-necked flask equipped with a gas inlet tube, mechanical stirrer and condenser (dry ice-acetone) provided with a nitrogen inlet was flushed with nitrogen and charged with 1.0 l of anhydrous liquid ammonia.
10.4 g (1.50 mol) of lithium wire (cut in 4 cm pieces) was added and the blue mixture was stirred slowly for 10 min at reflux. Then acetylene gas was passed into the reactor at a rate of ca. 700 ml/min. After ca. 1¼ hr when the blue color has been discharged, acetylene was introduced into the reactor for an additional 15 min at the same rate. Then the condenser and gas inlet tube were replaced by a thermometer and a 3-way connecting tube with dropping funnel and gas outlet.
100 ml of tetrahydrofuran was slowly added. Most of the ammonia was evaporated over 2½ hr by placing the bottom of the flask in an acetone bath. During the evaporation, an additional
700 ml of tetrahydrofuran was added form the dropping funnel, gradually replacing the ammonia. After the internal temperature reached +7° the white suspension was stirred at this temperature for 20 min. Then the solution prepared in Example 1 was added under nitrogen at 5°–7° to the well stirred lithium acetylide suspension over a period of 15 min. The solution was stirred at room temperature for 1 hr to give 1-[3-(1-methoxy-1-methylethoxy)-2,6,6-trimethyl-1-cyclohexen-1-yl]-3-methyl-1-penten-4-yn-3-ol in a tetrahydrofuran solution.

EXAMPLE 3

The solution prepared in Example 2 was poured into
750 g of ice water. After the addition of
10 mg of bromphenol blue to the two-phase mixture 6 N HCl was slowly added with stirring and icebath cooling (temp. <20°) till the color changed sharply from gree-blue to yellow (pH 3). A total of
560 ml of 6 N HCl was needed. Then an additional
10 ml of 6 N HCl was added, lowering the pH of the aqueous layer to pH 1.4. The mixture was stirred at room temperature for 40 min. Then
1.0 l of toluene was added, the organic layer separated, washed with
250 ml of saturated aqueous sodium bicarbonate and
500 ml of brine. The aqueous layer and washings were extracted in the same order with
400 ml of toluene, the combined organic phases dried (MgSO$_4$) and concentrated on a rotavap leaving
255  g  (109%)  1-(3-hydroxy-2,6,6-trimethyl-1-cyclohexen-1-yl)-3-methyl-1-penten-4-yn-3-ol as a crude yellow viscous oil (about 70% purity).

EXAMPLE 4

1-(3-oxo-2,6,6-trimethyl-1-cyclohexen-1-yl)-3-methyl-1-penten-4-yn-3-ol

A 5-l, three-necked flask equipped with mechanical stirrer, thermometer and reflux condenser was charged under nitrogen with
- 255 g (1 mol) of 1-(3-hydroxy-2,6,6-trimethyl-1-cyclohexen-1-yl)-3-methyl-1-penten-4-yn-3-ol prepared in Example 3,
- 0.7 l of acetone,
- 1.2 l of toluene and
- 80 g (0.39 mol) of aluminum isopropoxide. The mixture was stirred and heated at reflux for 2½ hr. The cooled flask content was poured into a mixture of
- 67 g (0.65 mol) of conc. (96%) sulfuric acid and
- 1.2 l of ice water and stirred for 5 min. The organic layer was washed with
- 300 ml of brine,
- 500 ml of saturated aqueous sodium bicarbonate and
- 300 ml of brine. The aqueous layer and washings were extracted in the same order with
- 400 ml of toluene. The combined organic phases were dried (MgSO4) and concentrated on a rotavap (40°/25 mm) leaving a viscous oil (290 g) which began to crystallize upon standing at room temperature. This material was dissolved in
- 350 ml of warm toluene and the solution allowed to cool to r.t.
- 500 ml of hexane was added with stirring. The clear yellow solution was stirred at room temperature overnight. The crystalline material was collected by suction filtration, washed with
- 400 ml of hexane-toluene 3:1 and dried at vacuo (const. weight) to afford
- 147.9 g (63.7%) of 1-(3-oxo-2,6,6-trimethyl-1-cyclohexen-1-yl)-3-methyl-1-penten-4-yn-3-ol as slightly yellow crystals, m.p. 86°–88°. The mother liquor was concentrated on on a rotavap and the residual oil (89 g) evaporatively distilled at 130°–165°/0.05 mm to give
- 69.8 g of a dark yellow distillate. This material was dissolved in
- 100 ml of toluene,
- 250 ml of hexane was added, the yellow solution was seeded and stirred at room temperature overnight. The precipitate was collected by filtration, washed with
- 75 ml of hexane-toluene 3:1 and dried at vacuo to afford a second crop of
- 17.9 g (7.7%) of 1-(3-oxo-2,6,6-trimethyl-1-cyclohexen-1-yl)-3-methyl-1-penten-4-yn-3-ol as white crystals, m.p. 86°–88°.

EXAMPLE 5

1-(3-Oxo-2,6,6-trimethyl-1-cyclohexen-1-yl)-3-methyl-1,4-pentadien-3-ol

A 2-l, three-necked flask equipped with mechanical stirrer, gas inlet and gas outlet was charged under nitrogen with
- 500 ml of methylene chloride and
- 8.25 g of Lindlar catalyst. A solution of
- 84 mg of 1,2-bis-(2-hydroxyethylthio)-ethane in
- 17 ml of methylene chloride, followed by
- 10 ml of triethylamine was added with stirring. Then a solution of
- 164.7 g (0.709 mol) of 1-(3-oxo-2,6,6-trimethyl-1-cyclohexen-1-yl)-3-methyl-1-penten-4-yn-3-ol in
- 350 ml of methylene chloride was added and the flask flushed with hydrogen. The mixture was then hydrogenated at room temperature and 790 mm Hg till hydrogen absorption was complete (8 hr). The mixture was filtered through a bed of silica, which was washed with methylene chloride. The clear light yellow filtrate was concentrated on a rotavap (35°/25 mm then 35°/2 mm) to afford
- 167.2 g (100.7%) of pure (>96%) 1-(3-oxo-2,6,6-trimethyl-1-cyclohexen-1-yl)-3-methyl-1,4-pentadien-3-ol as a yellow viscous oil.

EXAMPLE 6

1-(3-Hydroxy-2,6,6-trimethyl-1-cyclohexen-1-yl)-3-methyl-1-penten-4-yn-3-ol

A 1-l three-necked flask, equipped with a gas inlet tube, condenser (dry ice acteone) provided with gas outlet, thermometer and mechanical stirrer was charged under nitrogen with
- 440 ml of anhydrous liquid ammonia.
- 1.0 ml of 42% (wt/wt) aqueous potassium hydroxide was added dropwise to the vigorously stirred, refluxing ammonia. Then acetylene gas was passed into the reactor at a rate of 2.6 l/min. After 25 min. a solution of
- 5.80 g (27.8 mmol) of 4-(3-hydroxy-2,6,6-trimethyl-1-cyclohexen-1-yl)-3-buten-2-one in
- 5 ml of anhydrous ether was added to the mixture. The reaction mixture was stirred vigorously for 6 hr while acetylene was passed into the reactor at the same rate. Then
- 150 ml of anhydrous ether was added and the ammonia allowed to evaporate overnight.
- 50 ml of brine was added, the ether phase washed with 3×100 ml=
- 300 ml of brine. The aq. washings were reextracted with
- 100 ml of ether, the combined organic phases dried (MgSO4) and concentrated on a rotavap to yield
- 7.00 g of a light brown viscous oil (about 70% purity).

I claim:

1. A compound of the formula:

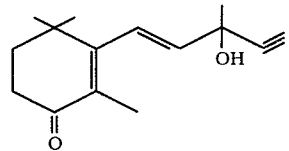

* * * * *